United States Patent [19]
Hoshino

[11] Patent Number: 5,265,616
[45] Date of Patent: Nov. 30, 1993

[54] BIOLOGICAL INFORMATION PROCESSING AND AUTOMATICALLY DISPLAYING APPARATUS

[75] Inventor: Nobuo Hoshino, Tokyo, Japan
[73] Assignee: Fukuda Denshi Kabushiki Kaisha, Tokyo, Japan
[21] Appl. No.: 841,595
[22] Filed: Feb. 25, 1992

[30] Foreign Application Priority Data
Nov. 13, 1991 [JP] Japan ............... 3-297106

[51] Int. Cl.⁵ .............................. A61B 5/04
[52] U.S. Cl. ...................... 128/696; 128/709; 128/710; 128/630; 128/905
[58] Field of Search ......... 128/696, 709, 710, 712, 128/672, 688, 670, 671, 736, 630, 632, 639, 905

[56] References Cited
U.S. PATENT DOCUMENTS

| | | | |
|---|---|---|---|
| 5,024,225 | 6/1991 | Fang | 128/96 X |
| 5,033,474 | 7/1991 | Varelis et al. | 128/696 |
| 5,123,420 | 6/1992 | Paret | 128/696 |

Primary Examiner—Lee S. Cohen
Assistant Examiner—Jeffrey R. Jastrzab
Attorney, Agent, or Firm—Merchant, Gould, Smith, Edell, Welter & Schmidt

[57] ABSTRACT

It is an object to project an alarm display device from a retracted position in the body of a biological information processing apparatus when it is determined that such a display is necessary according the results of date processed. The alarm display unit is set on the upper part of the apparatus. It is engaged to an enclosure so that there are two states; retracted/stored and projected. This alarm display unit comprises four alarm display devices, set in a line on the tip of the projected alarm display unit, which perform the displays indicating emergency in the case where it is projected. The alarm display unit is automatically projected when emergency has occurred on the subject and the condition is displayed by the alarm display device.

12 Claims, 6 Drawing Sheets

BIOLOGICAL INFORMATION PROCESSING AND AUTOMATICALLY DISPLAYING APPARATUS

BACKGROUND OF THE INVENTION

1. Field of the Invention

The present invention relates to a biological information processing apparatus, and more particularly, to a biological information processing apparatus capable of easily confirming, from a distance, whether collected biological information from a subject is within a predetermined fixed range.

2. Related Art

Recently, in order to assist a physician's diagnosis, a biological information processing apparatus which collects biological information, i.e. a subject's electrocardiogram (EKG) waveform, analyzes the collected information, and then outputs the result, is utilized extensively in medicine.

Some of these conventional apparatuses accommodate a device which supervises collected biological information from the subject, and then examines whether it is within a predetermined permissible range. In the case where the collected information is out of the range (in case of emergency), the apparatus outputs an alarm. As a form of alarm output, a sound alarm is produced from a built-in speaker.

There is also apparatus which can be optionally attached to an external pole. In this type of apparatus, the enclosure is metallic and the alarm pole can be attached to the apparatus structure by magnet force. The alarm pole device is connected to the enclosure by an interface cable. An AC power source for the device and a separate power source plug are required.

In the alarm pole device described above, there is need for to modification since the magnet cannot be used in attaching to a non-metallic enclosure. For example, attaching members are previously attached to the enclosure for connection. These attaching members are projected when the alarm pole device is not being used and require a large space above the apparatus in order to avoid catching the clothing of a passerby. In addition, the appearance of the apparatus is not sophisticated because of these attaching members. Further, in the case where two or more display devices are set up, these need to be arranged longitudinally. Accordingly, a length for the display devices become longer and there is the problem in the strength of the pole.

SUMMARY OF THE INVENTION

Accordingly, it is an object of the present invention to solve the above mentioned problems, that is, to provide a reliable apparatus capable of informing about the condition of a subject, which requires a small space above the enclosure, and an informing device therein will not be damaged even in transit.

According to the present invention, the foregoing object is attained by providing a biological information processing apparatus, comprising:

information collecting means for collecting biological information from a subject; analysis processing means for processing the analysis of the information collected by the collecting means; determination means for determining whether the result of the collected information is within a predetermined range; and a result display device which is engaged with one of the faces, except the bottom of the enclosure, so that the display device can be stored in the enclosure and projected, and said display device includes at least a first display means and a second display means arranged in a row on the projected result display device.

In accordance with the present invention as described above, no other elements are required for the configuration. Various kinds of information can be collected in a manner such that the result display device is projected from the apparatus enclosure according to the determined result and at least a first display means and a second display means are set in the determined result display device. Furthermore, since the result display device occupies only a small space and can be stored in the enclosure, the display device will not be damaged even by transport and it is possible to provide highly reliable biological information processing.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a device of the specification, illustrate embodiments of the invention and, together with the description, serve to explain the principles of the invention. In the drawings.

DESCRIPTION OF THE PREFERRED EMBODIMENTS

The preferred embodiment of the present invention will now be described in detail in accordance with the accompanying drawings.

In the present embodiment, a compact electrocardiogram (EKG) interpreter which collects and analyzes EKG waveforms is taken as an example. However, it is to be understood that the invention is not limited to this specific embodiment. For example, the present invention can be applied to any desired biological information processing apparatuses as well as the EKG interpreter.

Figure 1:
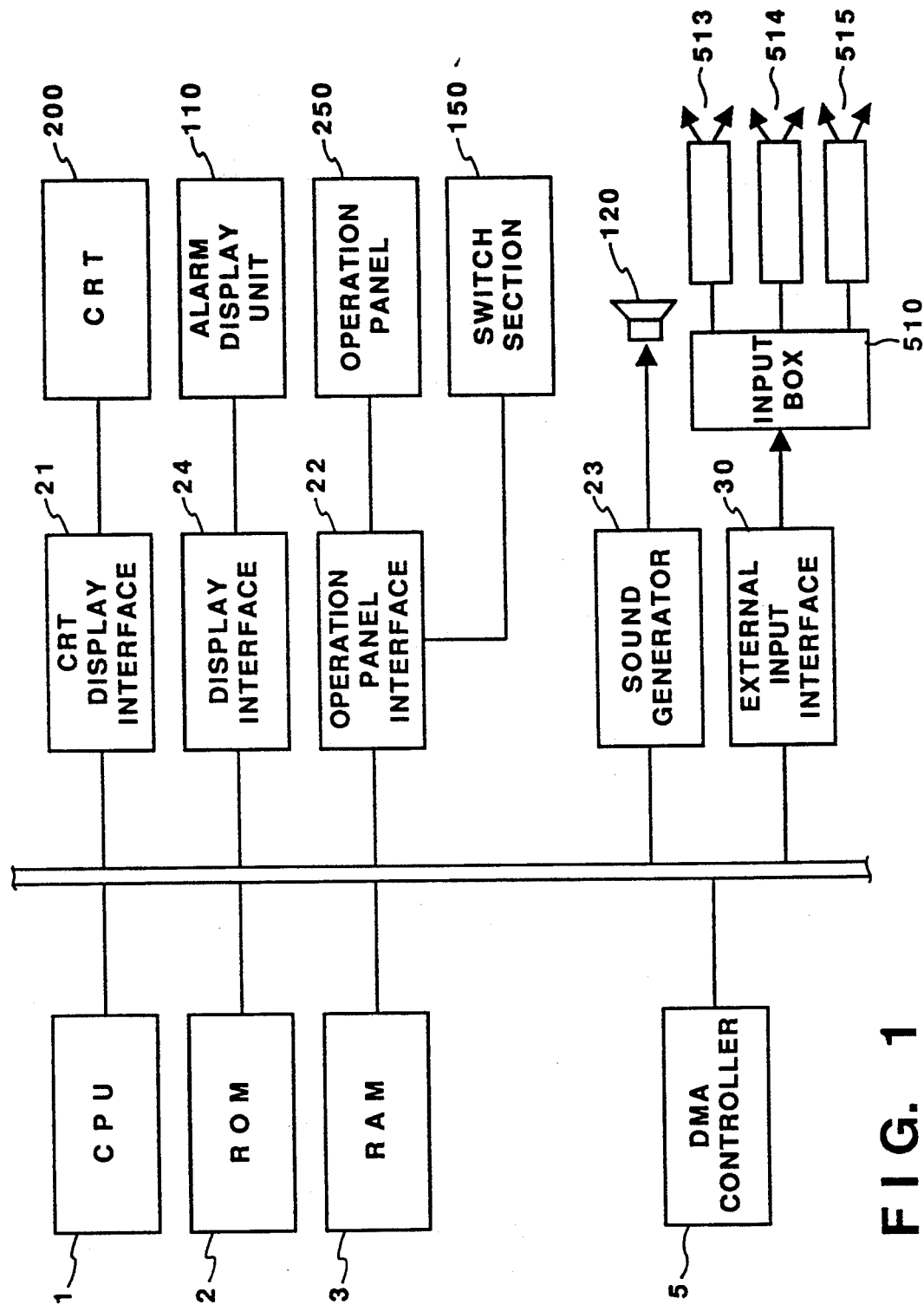
FIG. 1 is a block diagram which illustrates the constitution of a biological information processing apparatus according to the present invention.

FIG. 1 is a block diagram which illustrates the configuration of a biological information processing apparatus according to the present invention.

Figure 4:
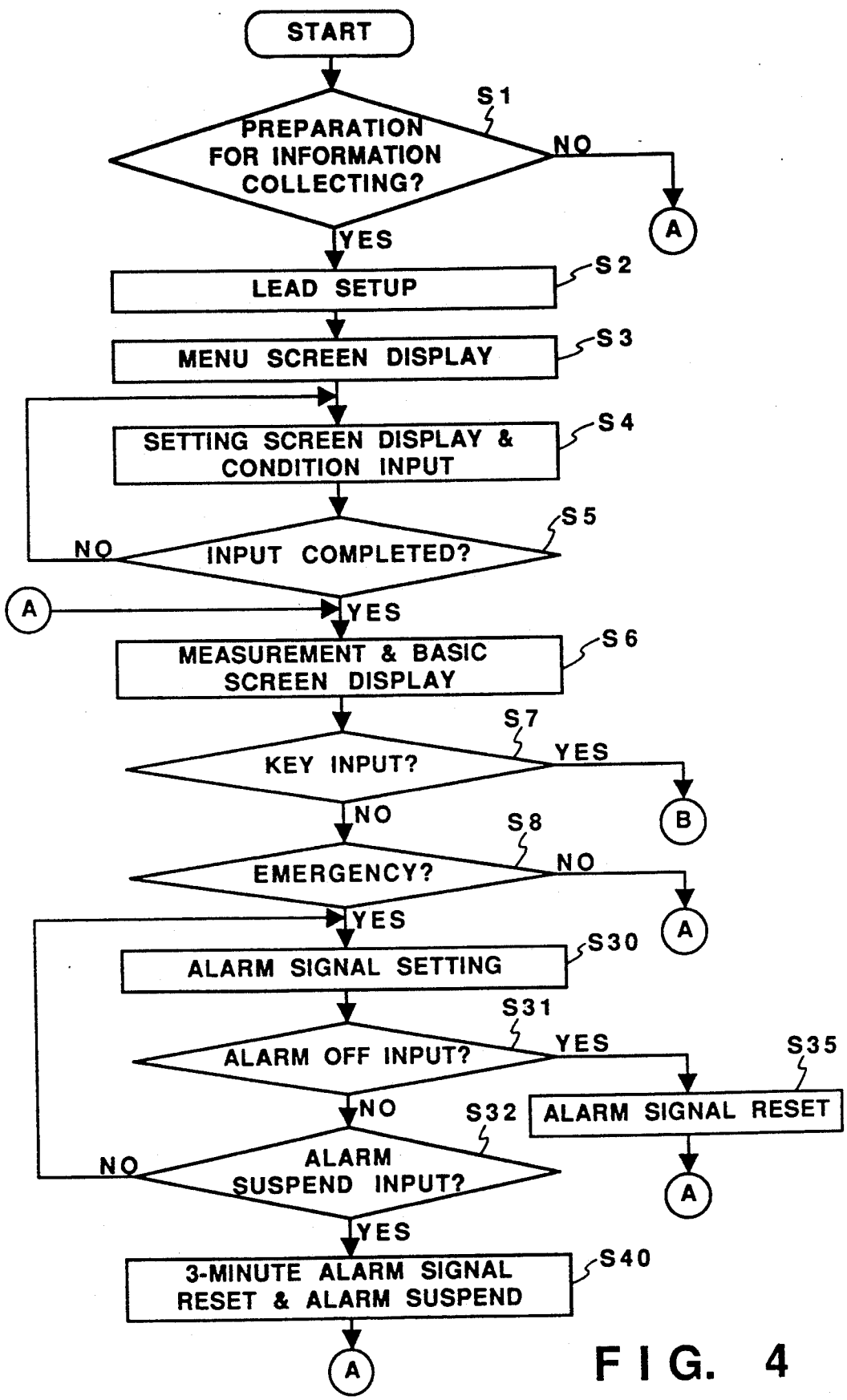
FIGS. 4 and 5 are flowcharts which illustrate the operations of the apparatus according to the present embodiment.

In the drawing, the reference numeral 1 refers to a CPU which controls the overall apparatus according to the programs shown in FIG. 4. The reference numeral 2 refers to ROM which stores fixed parameters used for the present embodiment and the above mentioned programs shown in FIG. 4. The reference numeral 3 refers to a RAM which temporarily stores processed data, and the reference numeral 5 refers to a DMA controller transmits to/from a connection input/output device in the DMA. The reference numeral 21 refers to a CRT display interface which controls the CRT display 200 and the reference numeral 22 refers to an operation panel interface which operates the interface with the operation panel 250 and with the switch section (key board) 150. The reference numeral 23 refers to a sound generator which generates a sound signal outputted from the speaker 120 and the reference numeral 24 refers to a display interface which controls an alarm display of the alarm display unit. The reference numeral 30 refers to an external input interface with the input box 510 and converts the collected biological information from analog to digital signals.

The reference numeral 110 refers to a planer alarm display unit having a plurality of alarm devices near the tip of the display unit, which indicates that emergency has occurred on the subject. When the display unit is not used, it is stored in the enclosure, while it is used, it pivots up to a vertical position on the enclosure so that it can be observed from a distance. The movement to vertical position of the display unit 110 is automatic while retraction of (storing) this display into the enclosure is manual.

The reference numeral 120 refers to the speaker. The reference numeral 150 represents a switch section (key board) which provides for permanent access to necessary inputs, i.e. alarm reset and calling for main menu screen when various different display screens on the CRT are in use, and the reference numeral 200 refers to a CRT display. The reference numeral 250 refers to an operation panel which is set on the surface of the CRT display 200. The operation panel 250 is a pressure sensitive touch panel on which the coordinates and key functions correspond to function displayed on the CRT. Furthermore, since the operation panel 250 comprises of a transparent electrode, a display of the CRT 200 can be clearly viewed.

The reference numeral 510 refers to an input box which is an analog input interface, and the reference numerals 513–515 refer to biological amplifier modules (induction codes) that connect to the input box 510. The biological amplifier modules 513–515 can be connected to an electrode for an EKG, a blood pressure transducer, etc., not limiting the present invention to the two above mentioned inputs. It can be set up so that the signal from the electrode can be sent by radio waves to a telemeter, which can be built into the input box 510. In this configuration, the induction device and the input box 510 do not have to be connected by a signal wire and it reduces the physical burden on subject.

Furthermore, the apparatus is capable of utilizing a device for reading the temperature of the subject and a device that counts the number of respiration per minute of the subject. Accordingly, various kinds of biological information can be collected by the apparatus according to the present invention.

Figure 2:
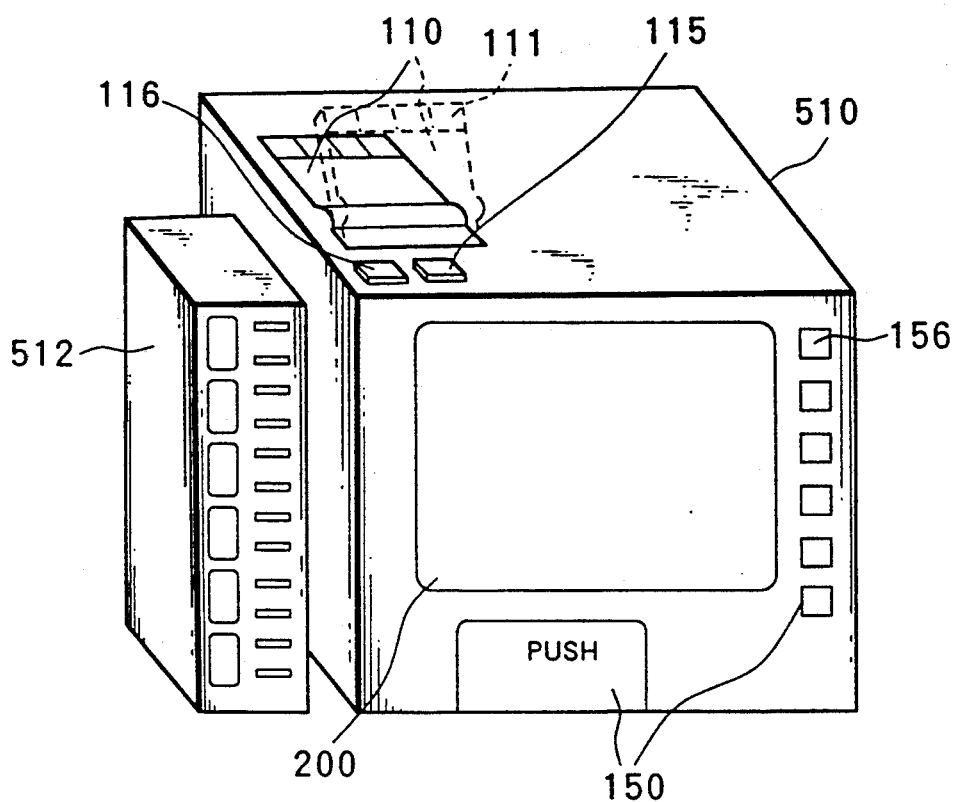
FIG. 2 is a view of exterior of the apparatus according to the present embodiment.

FIG. 2 is a illustration of exterior of the apparatus according to the present embodiment. In FIG. 2, the reference numeral 110 refers to the alarm display unit. The solid line illustrates the state where the alarm display unit 110 is retracted in the upper part of the enclosure and the dashed line illustrates the state where it is pivoted to a standing position. The reference numeral 111 represents a group of alarm display devices which are positioned at the tip of the alarm display unit 110. The alarm display device 111 comprises four alarm display devices. Diodes, which light up either in red, yellow, green, or any other color, are built into each device.

The reference numeral 115 refers to a parameter key which selects a supervising parameter to be displayed by the alarm display device 110. The parameter key 115 is capable of changing the parameter to be displayed, i.e. the blood pressure, respiratory trouble, or EKG every time a parameter key is depressed. The reference numeral 116 refers to an "auto" key which switches from the automatic mode to the non-automatic mode when the auto key is depressed or vise versa. The operation of the auto key will be described in detail later. The general description of the automatic mode, however, is that the alarm display unit 110 pivots to a standing position on the enclosure when an emergency has occurred, and the alarm display device 111 is lit with the color corresponding to the subject's condition. On the other hand, in the non-automatic mode, when the alarm display unit 110 has been previously moved to the upright position, the alarm display device 111 is lit with the color corresponding to the subject's condition. When the alarm display device 111 is being retracted, the alarm display unit 111 is not lit. When the alarm display unit 110 is retracted while in the non-automatic mode, the alarm display devices 111 will not be lit even when an emergency has occurred.

Figure 3:
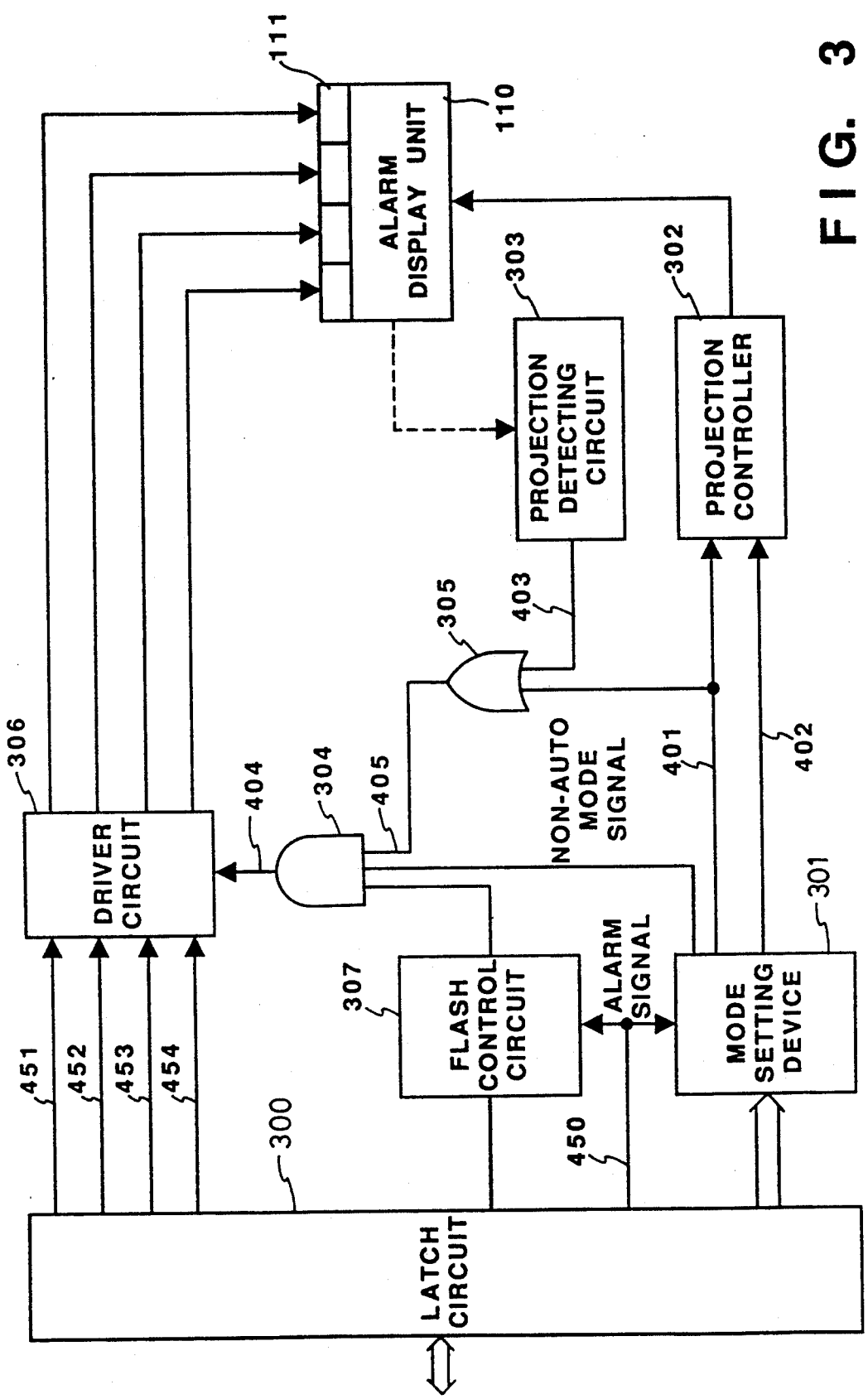
FIG. 3 is a detailed view illustrating the constitution of the display interface of the apparatus according to the present invention.

FIG. 3 is a detailed view which illustrates the configuration of the display interface 24 of the apparatus according to the present invention. In the drawing, the reference numeral 300 refers to a latch circuit which receives a control signal from the CPU 1 (to be described later). The reference numeral 301 refers to a mode setting device which retains information such as whether the alarm display mode is set to "auto", "semi-auto", or "non-auto mode". The mode setting device 301 outputs an auto signal 401 in the case where it is set to the "auto" mode. In the case where it is set to the "semi-auto" mode, it outputs a semi-auto signal 402. The reference numeral 302 refers to a projection controller which projects the alarm display unit 110, in the case where the auto signal 401 or the semi-auto signal 402, in conjunction with the alarm signal 450, which would indicate that emergency has occurred on the subject, are outputted.

There are various ways to project the alarm display unit 110. One way is that a spring is situated at the place where the alarm display unit is retracted in the enclosure and the alarm display unit 110 is forced a fixed pressure until it is in the locked upright position. When it is to be stored (retracted) in the enclosure, stoppers (i.e. hooks) can be set so that the alarm display unit 110 is engaged with the stoppers.

Another way is that the alarm display unit 110 can be pushed into the enclosure and pulled up under the fixed pressure.

Another way is that the projection controller 302 releases the retracted state by, i.e. a solenoid control and the alarm display unit 110 can be projected by spring pressure.

Another way is that the alarm display unit 110 is forcefully pulled up by a plunger.

In addition to the above described ways, if a setup is capable of retracting and projecting the alarm display unit 110, it can be adopted to the apparatus.

Furthermore, referring to FIG. 3, the reference numeral 303 refers to a projection detecting circuit and outputs a "standing" signal 403 when the alarm display unit 110 is being pivoted to the standing position. The reference numeral 304 refers to the light emitting control gate which controls a light emitting of LED in the alarm display device 111 and outputs a light emitting control signal 404. The reference numeral 305 refers to an OR circuit which outputs an output signal 405 in the case where either the auto signal 401 or the projection signal 403 is activated. The reference numeral 306 refers to a driver circuit which lights up the alarm display device 111 according to a light emitting color control signal. This control signal is given when the light emitting control signal 404 from the light emitting control gate 301 is "1". The light emitting color control signal rotates a kind of signal which displays the emergency according to the depression of the parameter key 115 previously described. The reference numeral 307 refers to a flash control circuit which controls whether, the alarm display device 111 should be constantly lit or flashing.

The CPU 1 outputs an alarm signal 402 in the case where the collected EKG information from the subject is out of the permissible range in the alarm setting process (to be described later).

The flash control circuit 307 is set up so that a clock signal is generated within the circuit and the alarm signal is outputted in the fixed cycle. However, it can be set up that a QRS synchronizing signal, which becomes "1" when the QRS of the collected EKG signal is detected, is received and this signal is set as the standard. Then, the alarm signal is outputted based on this standard in the fixed cycle. In the way described above, when the QRS synchronizing signal is received, the alarm display is flashed. On the other hand, when the QRS synchronizing signal is not received, the alarm display is lit. Accordingly, the condition of the subject is easily confirmed from a distance.

In accordance with the present embodiment, each of the four display devices of the alarm display device 111 accommodates LEDs for red, yellow, green, or any other color and the CPU 1 changes the color according to the subject's condition. For example, when the subject's condition is stable, the alarm display is in green. When the subject's condition requires relatively urgent attention, the display is in yellow. The condition is in case of emergency, the display is in red. Accordingly, the condition of the subject is easily recognized from a distance. It is also possible to set it up so that the color of the alarm display device 111 can be changed according to the problem, i.e. abnormality in the blood pressure, the EKG, or in respiration. Furthermore, the timing of flashing in the alarm display device 111 is changed and in which signal the emergency has occurred can be displayed. For example, a frequency of flash can be changed according to a value of the blood pressure.

Figure 5:
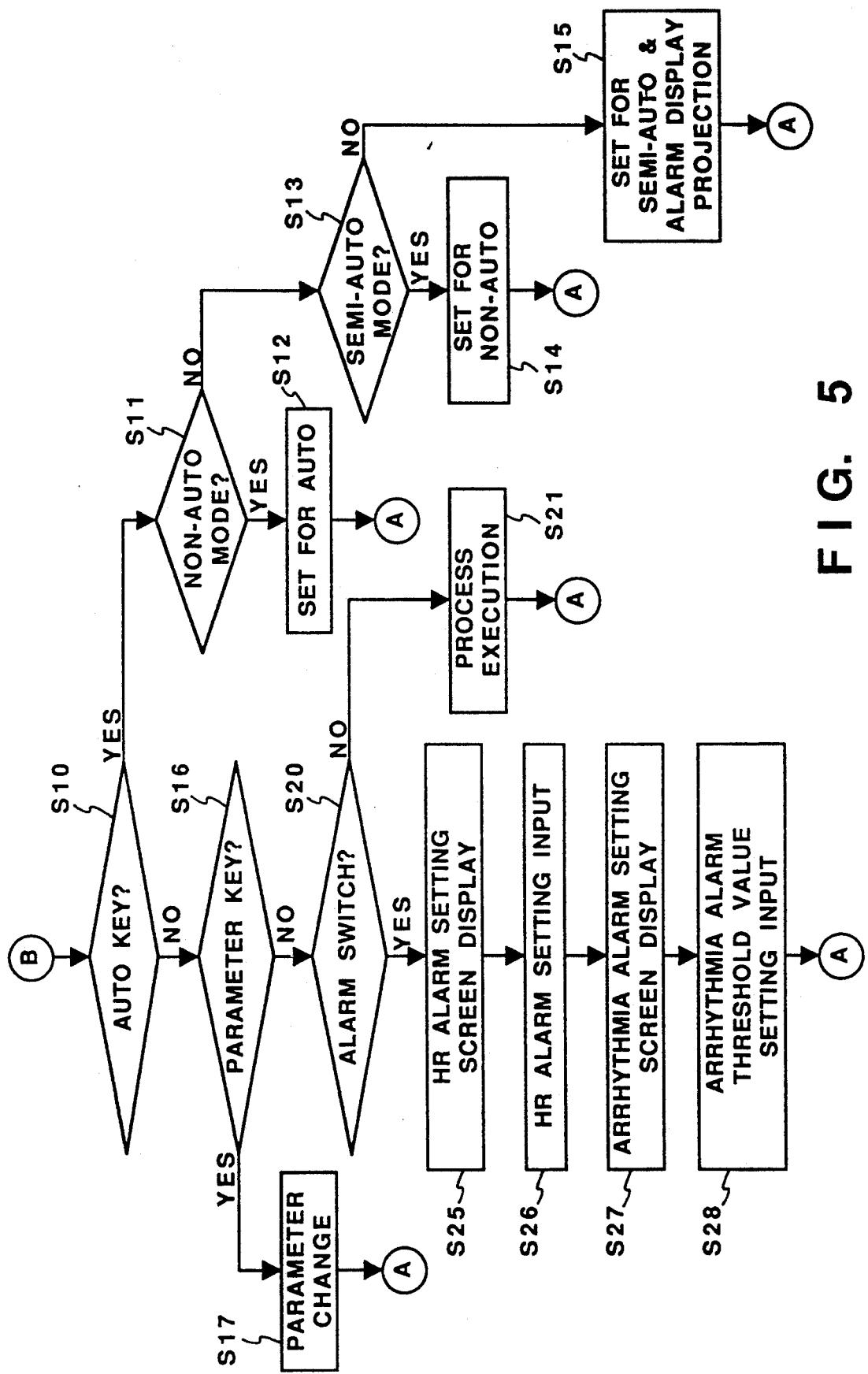

In accordance with the above described configuration, information collecting control and analysis control are now described along with the flowcharts in FIGS. 4 and 5.

In step S1, it is determined whether a preparation process for the information collected from the subject should be performed. In the case where the preparation process is selected, the process proceeds to step S2. In step S2, each electrode of the biological amplifier modules (induction code) 513-515 connected to the input box 510 is attached to the appropriate part of the body and a highly directional microphone is set in the appropriate position. Since the technique of attaching electrode to the subject, and the use of highly directional microphone are well known, a detailed description is omitted here.

Once the preparation for measurement is completed, a menu switch 156 is pushed down in step S3 and a main menu screen is displayed on the CRT 200. In steps S4 and S5, various kinds input screens can be selected from the main menu screen and the necessary conditions are then inputted for the setting. After the conditions are inputted, the process proceeds from step S5 to step S6. In step S6, the position of 251 of the operation panel 250 which is the basic screen key at this time is pushed down by an operator and the measured waveform from the induction code and the analyzed result for the waveform are displayed. Then, in step S7, it is examined whether there is a key input. In the case where there is no key input, in step S8, an alarm is set, and the measured information is examined if it is within the alarm setting threshold value. In the case where it is within the alarm setting threshold value, i.e. the condition is stable, the process returns to step S6 and the basic screen is displayed until either a key is depressed or an emergency has occurred on the subject.

Figure 6:
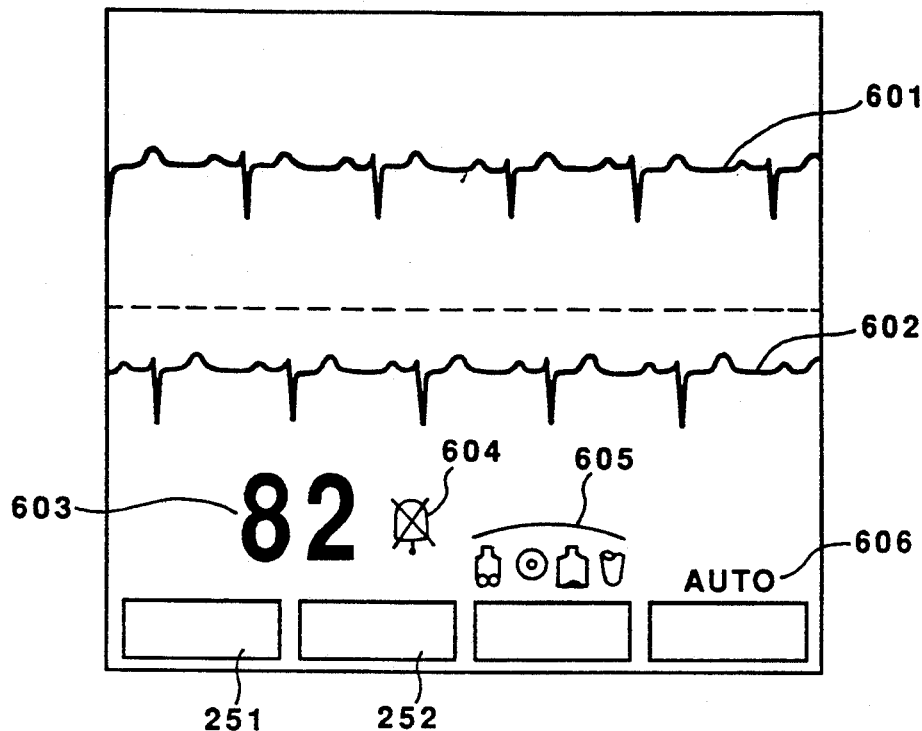
FIG. 6 is a view which illustrates the basic screen according to the present embodiment.

One of the examples for a basic screen of the CRT 200 is illustrated in FIG. 6. In the drawing, the reference numerals 601 and 602 refer to measured EKG waveforms and the reference numeral 603 refers to the heart rate. The reference numeral 604 refers to an alarm-off mark which is changed to an alarm threshold value when an alarm setting (to be described later) is performed and the alarm is set to "on". The reference numeral 605 refers to a display area for character sign message. Each kind of analyzed result can be displayed in accordance with the characters corresponding to the result desired, i.e. EKG, temperature, etc. The reference numeral 606 refers to a message display which indicates that the alarm display mode is set to the auto mode in the present state.

In this state, if there is a key switch input, the process proceeds from step S7 in FIG. 4 to step S10 in FIG. 5 where it is determined whether the input was for the auto key 116. If it is the input for the auto key 116, the process proceeds to step S11 where it is examined whether the current setting mode of the mode setting device 301 is the non-auto mode. If it is set to the non-auto mode, the process proceeds to step S12 where the mode setting device 301 is set to auto mode. The process then returns to step S6.

In step S11, if the current mode is not set to the non-auto mode, the process proceeds to step S13 where it is determined whether the mode setting device 301 is set to semi-auto mode. If it is set to the semi-auto mode, the process proceeds to step S14 where the mode device 301 is set to the non-auto mode which does not perform an alarm display on the alarm display unit 110 even in case of the emergency. The process then returns to step S6. In this case, it is preferable for the of the alarm display unit 110 to be retracted into the enclosure.

On the other hand, in step S13, if the mode setting device 301 is not set to semi-auto mode, the mode at this time should be the auto mode. Therefore, it has to be changed to semi-auto mode in step S15. Accordingly, the mode setting device 301 outputs a semi-auto signal 402, and instructs the projection controller 302 to pivot the alarm display unit 110 to the upright position. The projection controller 302 projects the according to this instruction. The process then returns to step S6.

In step S10, if the input was not for the auto key 116, the process proceeds to step S16 where it is examined whether the input is for a parameter key 115. If it is for a parameter, the process proceeds to step S17 where a display item is selected. The process then returns to step S6 where the basic screen is displayed. On this screen, all display items (items to be displayed and not to be displayed) are listed on the screen of the CRT 200 and the item to be displayed is selected when a part of the screen which corresponds to the display item of the operation panel is touched. Accordingly, the alarm display items to be displayed in case of emergency are also selected by a simple procedure.

On the other hand, in step S10, if the input is not for the parameter key 115, the process proceeds to step S20 where it is examined whether it is for the alarm switch (the reference numeral 251 in the alarm setting screen). If it is not for the alarm switch 251, the step proceeds to step S21 where a process corresponding to the input switch is executed. The process then returns to step S6. For example, suppose that it was the input for waveform suspension/release switch 252. The current displayed waveform is frozen on the CRT 200. Then, the process returns to step S6. On the other hand, in the case where the waveform is not displayed on the CRT and the waveform suspension/release button is pressed, the CRT returns to real-time waveform display. Then the process returns to step S6.

Figure 7:
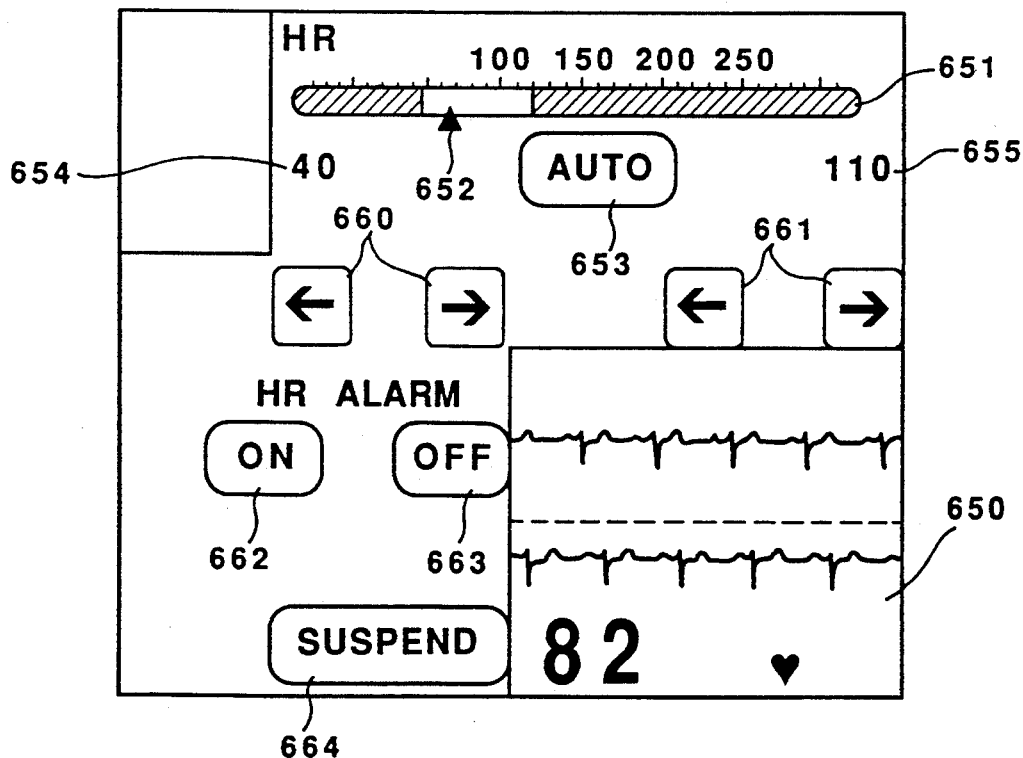
FIG. 7 is a view which illustrates an example of the display of the alarm set screen according to the present embodiment.

In step S20, in the case where the input is for the alarm switch 251, the process proceeds to step S25 where a heart rate alarm setting screen is displayed on the CRT 200, where the apparatus waits for input with respect to the heart rate alarm maximum and minimum values. Then, in step S26, the heart rate alarm setting input is performed. One of examples for the heart rate alarm setting screens is shown in FIG. 7.

In the drawing, the reference numeral 650 refers to a display area for compressed waveform of the measured EKG waveform from the subject. It is set up that the subject's condition can be confirmed even when the alarm setting process is being processed. That is, according to the present invention, the subject's condition can be supervised at the setting input since the compressed waveform of the measured EKG waveform is displayed, i.e. at the bottom of the right corner of the screen even when a setting guidance screen is displayed. The reason why the screen is set up so that the basic screen and a compressed waveform which is similar to the original waveform are simultaneously supervised is that the operator who is operating the setting process is generally close enough to the apparatus to observe the compressed waveforms. Accordingly, it is possible to avoid the problem in which the waveform, when the waveform is not compressed and only a short time sample is displayed on the screen, a change cannot be recognized.

In the same drawing, the reference numeral 651 refers to a display area for heart rate and the current heart rate is pointed out by the mark Δ of the reference numeral 652.

The reference numeral 653 refers to an alarm threshold value auto setting instruction switch, the reference numeral 654 refers to an alarm minimum threshold value display, and the reference numeral 655 refers to an alarm maximum threshold value display. The threshold of the above described switches 653–655, 660 and 661 can be increased by the "←" switch input, and decreased by the "→" switch input.

The reference numeral 662 refers to an alarm ON switch. In the case where this switch is depressed and the alarm threshold value is out of the range, the alarm is given.

The reference numeral 663 refers to an alarm OFF switch. In the case where this switch is depressed, the emergency is not informed even when the emergency has occurred. The reference numeral 664 refers to an alarm interruption switch. The alarm is interrupted for approximately 3 minutes after the input from switch 664.

The alarm setting input is set to the current heart rate (+40 BPM, −20 BPM) from the setting screen shown in FIG. 7 when the auto switch display position is depressed. Since the alarm threshold value is either increased or decreased by 10 BPM unit every time the switch input is depressed, an alarm threshold value can be set to any desired value. In the present embodiment, the maximum heart rate range limit can be freely set when the value is increasing by 10 BPM unit, while the minimum heart rate range limit can also be freely set when the value is decreasing by 10 BPM. Furthermore, the heart rate alarm can be switched on/off or interrupted when each corresponding switch is pushed down.

Accordingly, the setting input for the heart rate alarm is completed, the process proceeds to step S27 in FIG. 5 where an arrhythmia alarm setting screen is displayed by the operation from the menu screen. In step S28, the setting input for the arrhythmia alarm is performed. In this step, a kind of analyzed arrhythmia is selected and an alarm threshold value is set.

In the above description, only the EKG is described as an example. However, when there is another parameter, there should be a setting screen which is similar to the heart rate alarm and each setting screen has instructions for alarm ON/OFF, alarm interruption, and the like. The process then proceeds to step S6. Whenever the basic screen key is depressed, the process returns to step S6. However, if the key is not fixed period of time (i.g. 1 minute).

In a loop process from step S6 to step S8 in FIG. 4, in the case where the measured value is out of the alarm setting threshold value, which indicates that an emergency has occurred, the process proceeds from step S8 to step S30 where the alarm signal 450 in FIG. 3 is set and the flash control signal to the flash control circuit 307 is outputted when the flash display is required. In the case where the auto signal 401 is outputted, the projection control circuit 302 projects the alarm display device 111 from the main unit of the apparatus. In the case where the alarm display device 111 has been already projected, the alarm display device 111 corresponding to the alarm signal 450 and the flash signal from the flash control circuit 307 or the alarm item signals 451–454 is lit in the designated color and flashed if required. In this case, as described above, the light emitting can be controlled when the QRS synchronizing timing is synchronized. When the QRS synchronizing signal is not detected, the alarm display device 111 stays on. Accordingly, the subject's condition can be confirmed by this display light.

Furthermore, in case of emergency, the sound generator 23 is activated as well as the alarm signal 450 and the alarm sound can be outputted from the speaker 120. It ensures that warning of the emergency can be recognized.

Accordingly, in the case where an emergency is informed in step S30, the processes proceed to steps S31 and S32 where it is determined whether the operator recognized the alarm and inputted the alarm OFF switch 663 or whether the alarm interruption switch 664 is inputted. If there is neither of these inputs, the process returns to step S30 and the alarm is continuously given.

According to the present embodiment, it is possible that only the alarm sound is stopped when the alarm reset key 156 shown in FIG. 2 is pushed down without operating through the display screens.

In the case where the alarm OFF switch 663 is inputted in step S31, the process proceeds to step S35 where the alarm signal 450 is reset and the state where the alarm is being given is suspended. The process then returns to step S6.

In the case where the alarm interruption switch 664 is pressed, the process proceeds from step S32 to step S40 where the alarm signal 450 is reset, a timer circuit (not shown) is activated, the timer is set for 3 minutes. The alarm signal 450 is given again after 3 minutes and the process returns to step S6.

According to the present invention, the fact that an emergency occurred on the subject can be quickly noticed even from a distance, without any additional elements, by the alarm display devices 111 of the alarm display unit 110 and the conventional sound alarm output. Further, in the case where a plurality of the apparatuses like the one in the present embodiment are arranged in one supervising room, it is possible to easily identify at which the apparatus the emergency has occurred and to cope with a quick treatment.

Further, condition of each patient (subject) can be grasped even from the outside of a hospital room and when, in particular, the patient with a heart deficiency has emergency, he/she can be quickly and accurately treated.

The present invention is particularly advantageous because of the following reasons:

(1) It is possible to provide an apparatus which is less expensive than the apparatus which has to attach the additional alarm display;

(2) Since the alarm display unit does not have to be attached to the enclosure by additional elements, it can be retracted if it is not needed and automatically projected if an emergency has occurred. Accordingly, in the portable apparatus accommodating a 5-inch screen according to the present embodiment, the alarm display unit is not disturbed in transport. The same advantage can be obtained even in a stationary type;

(3) Since the connection with the alarm display unit 110 by the cable is not required and the connection cable is not exposed to outside of the enclosure, a connection error possibly is eliminated and the appearance is sophisticated; and (4) Since the visual alarm display unit which is in a form of plate is previously attached to the apparatus and designed for maximum visuality, only a small space for a plurality of display devices is occupied and the alarm display unit can be physically strong enough.

As described above, in accordance with the present invention, an emergency in the condition of a patient with a heart deficiency is quickly noticed even from a distance and appropriate treatment can be provided.

Furthermore, the diagnosed result can be informed when i.e. the alarm display devices are projected from the enclosure based on the result without attaching any additional structural elements. Accordingly, only a small space above the enclosure is occupied and various kinds of information can be obtained when at least a first display means and a second display means are set in the result display device.

As many apparently widely different embodiments of the present invention can be made without departing from the spirit and scope thereof, it is to be understood that the invention is not limited to the specific embodiments thereof except as defined in the claims.

What is claimed is:

1. A biological information processing apparatus, comprising:
    information collecting means for collecting biological information from a subject;
    analysis processing means for processing an analysis of the collected biological information by said information collecting means;
    determination means for determining whether or not a result of the analysis by said analysis processing means is within a predetermined range;
    alarm display means for displaying an alarm of the analysis; and
    means for attaching the alarm display means to an outer surface, except a bottom surface, of the apparatus, the alarm display means being retracted into the apparatus through the outer surface when no alarm of analysis is displayed, and being capable of automatically projecting from the apparatus through the outer surface when the alarm display means displays the alarm of the analysis, and said alarm display means including at least one display means capable of indicating a status of the result of the analysis.

2. The biological information processing apparatus according to claim 1, wherein said alarm display means is mounted on a top portion of the apparatus.

3. The biological information processing apparatus according to claim 1, wherein said alarm display means is prohibited to display indicating the result when the display means is stored in the apparatus and said alarm display means indicates that measured information by said determination means is out of the predetermined range when it is projected.

4. The biological information processing apparatus according to claim 1, comprising:
    display device control means for controlling the alarm display means to be projected from the apparatus when said determination means determines that measured information is out of the predetermined range.

5. The biological information processing apparatus according to claim 4, further comprising:
    a first control mode in which said display device control means controls the alarm display means to be projected from the apparatus when said determination means determines that the measured information is out of the predetermined range; and
    a second control mode in which the display device control means controls said alarm display means not to display when said alarm display means is stored in the apparatus and controls to indicate that the measured information is out of the predetermined range when the alarm display means is being projected.

6. The biological information processing apparatus according to claim 5, comprising:

assignment means capable of inputting an instruction to assign a control mode selecting from the first control mode and the second control mode so that the apparatus is operated in said control mode.

7. The biological information processing apparatus according to claim 1, wherein said alarm display means is capable of displaying in a plurality of colors and, when said determination means determines that a measured information is out of the predetermined range, a display color of a measured object of the subject is changed.

8. The biological information processing apparatus according to claim 1, wherein said alarm display means is capable of changing a timing of flash and when said determination means determines that measured information is out of the predetermined range, a flashing frequency on the alarm display means is changed according to a measured object of the subject.

9. The biological information processing apparatus according to claim 8, wherein said alarm display means is capable of flashing synchronous with a QRS detection of an electrocardiogram signal.

10. The information processing apparatus according to claim 1, wherein the information collecting means collects information at least on electrocardiogram, temperature, number of respirations per minute, and blood pressure.

11. The biological information processing apparatus according to claim 1, wherein said determination means is capable of performing analysis using different predetermined range values according to an information object to be collected.

12. A biological information processing apparatus, comprising:

information collecting means for collecting biological information from a subject;

analysis processing means for processing an analysis of the collected biological information by said information collecting means;

determination means for determining whether or not a result of the analysis by said analysis processing means is within a predetermined range;

alarm display means for displaying an alarm of the analysis;

means for attaching the alarm display means to an outer surface, except a bottom surface, of the apparatus, the alarm display means being retracted into the apparatus, the alarm display means being retracted into the apparatus through the outer surface and being capable of being projected from the apparatus through the outer surface, and said alarm display means including at least one display means capable of indicating a status of the result of the analysis; and display control means for operating in a first control mode which controls the alarm display means from a retracted position to a projected position when said determination means determines that measured information is out of a predetermined range, and a second control mode which controls said alarm display means not to display when said alarm display means is in the retracted position and controls said alarm display means to display when said measured information is out of a predetermined range and when the alarm display means is in the projected position.

* * * * *